US012702352B2

(12) United States Patent
Kivilinna et al.

(10) Patent No.: US 12,702,352 B2
(45) Date of Patent: Aug. 11, 2026

(54) DYNAMIC LIGHT EMITTING DIODE VOLTAGE CONTROL FOR WEARABLE DEVICES

(71) Applicant: Oura Health Oy, Oulu (FI)

(72) Inventors: Jussi Heikki Tapio Kivilinna, Oulu (FI); Tero Jääskö, Oulu (FI); Samuel Juho Verti Poikola, Oulu (FI); Mikko Pellervo Tuohimaa, Kempele (FI); Jaakko Iiro Juhani Kukkohovi, Kempele (FI)

(73) Assignee: Oura Health Oy, Oulu (FI)

( * ) Notice: Subject to any disclaimer, the term of this patent is extended or adjusted under 35 U.S.C. 154(b) by 0 days.

(21) Appl. No.: 18/625,753

(22) Filed: Apr. 3, 2024

(65) Prior Publication Data

US 2025/0311969 A1 Oct. 9, 2025

(51) Int. Cl.

| | |
|---|---|
| ***A61B 5/00*** | (2006.01) |
| ***A61B 5/024*** | (2006.01) |
| ***H05B 45/30*** | (2020.01) |

(52) U.S. Cl.

CPC ........ *A61B 5/4812* (2013.01); *A61B 5/02427* (2013.01); *A61B 5/4809* (2013.01); *A61B 5/681* (2013.01); *H05B 45/30* (2020.01); *A61B 2560/0214* (2013.01)

(58) Field of Classification Search

CPC ...... H05B 45/30; A61B 5/02427; A61B 5/681
See application file for complete search history.

(56) References Cited

U.S. PATENT DOCUMENTS 5,590,652 A * 1/1997 Inai .................... A61B 5/02416 600/323
7,573,729 B2 * 8/2009 Elferich ............... H05B 45/382 315/210
8,174,482 B1 * 5/2012 Yeung .................. G09G 3/3406 345/87

(Continued)

FOREIGN PATENT DOCUMENTS

DE 60125326 T2 9/2007

OTHER PUBLICATIONS

German Search Report issued in DE Application No. 202025101614.1, dated Jan. 21, 2026, 9 pages (4 pages of Original Document, 5 pages of Translation Document).

*Primary Examiner* — Oommen Jacob
(74) *Attorney, Agent, or Firm* — ArentFox Schiff LLP

(57) ABSTRACT

Methods, systems, and devices for voltage control for wireless devices are described. The described techniques may enable a wearable device to dynamically select and adjust the starting input voltage (e.g., VLED) for one or more light emitting diodes (LEDs). In particular, a wearable device may dynamically determine the starting input voltage of the LEDs based on an LED configuration to be used by the LEDs, and a threshold anode line voltage to power the LEDs. The LED configuration may include parameters or characteristics of the LEDs to perform physiological measurements. The wearable device may determine an LED configuration that may be used to collect physiological data, and may perform simulations to model the voltage of the anode line throughout a measurement interval based on the LED configuration. The wearable device may determine a VLED that may maintain a voltage of the anode line above the threshold anode line voltage.

20 Claims, 6 Drawing Sheets

(56) References Cited

U.S. PATENT DOCUMENTS

| | | | | |
|---|---|---|---|---|
| 9,636,036 | B2 * | 5/2017 | Khalfallah | A61B 5/6801 |
| 2005/0187447 | A1 * | 8/2005 | Chew | A61B 5/14551<br>600/323 |
| 2014/0121471 | A1 * | 5/2014 | Walker | A61B 5/1128<br>600/479 |
| 2015/0018649 | A1 * | 1/2015 | Lisogurski | A61B 5/14552<br>600/323 |
| 2017/0099711 | A1 * | 4/2017 | Polley | A61B 5/02427 |
| 2018/0184979 | A1 * | 7/2018 | Hanks | A61B 5/02438 |
| 2018/0353074 | A1 * | 12/2018 | Kruiskamp | A61B 5/02416 |
| 2020/0138379 | A1 * | 5/2020 | Huiku | A61B 5/7221 |

* cited by examiner

Identify a light-emitting configuration usable by one or more light-emitting components of the wearable device to acquire physiological data from a user throughout a measurement interval, the light-emitting configuration comprising a drive voltage associated with the one or more light-emitting components, a current provided to the one or more light-emitting components during the measurement interval, a measurement pattern throughout the measurement interval, or any combination thereof

605

Determine a minimum anode voltage of an anode line coupled with the one or more light-emitting components that enables the one or more light-emitting components to acquire physiological data throughout the measurement interval based at least in part on the light-emitting configuration, wherein an anode voltage of the anode line is based at least in part on an input voltage of a power input line coupled with a power supply of the wearable device

610

Calculate, for the light-emitting configuration, a starting input voltage of the power input line based at least in part on the minimum anode voltage

615

Cause a power supply (e.g., the battery, a converter, or both) to charge the anode line to at least the starting input voltage prior to the measurement interval

620

Acquire physiological data from the user during the measurement interval using the one or more light-emitting components based at least in part on charging the anode line to at least the starting input voltage

625

600

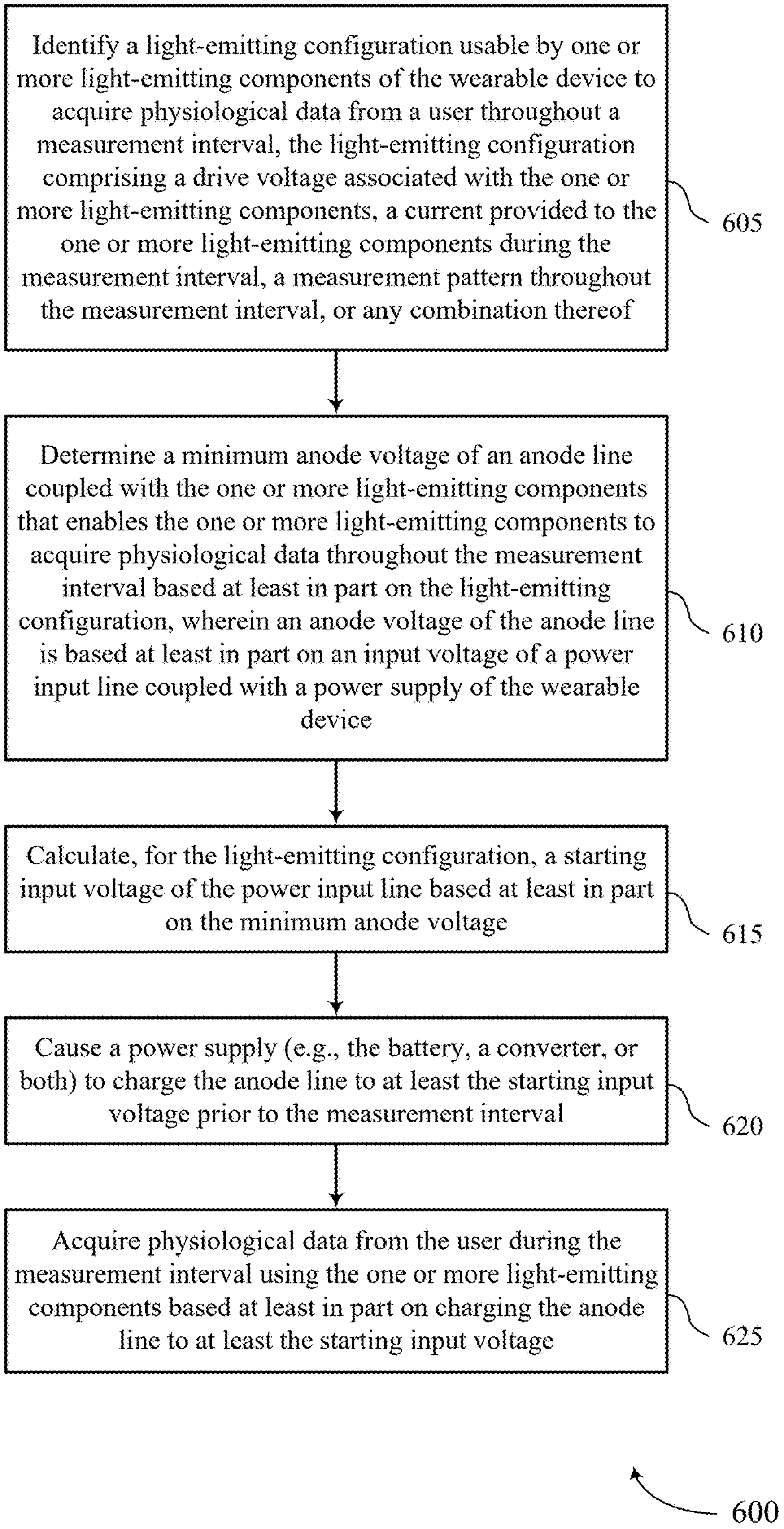

FIG. 6

DYNAMIC LIGHT EMITTING DIODE VOLTAGE CONTROL FOR WEARABLE DEVICES

FIELD OF TECHNOLOGY

The following relates to wearable devices and data processing, including dynamic light emitting diode (LED) voltage control for wearable devices.

BACKGROUND

Some wearable devices may be configured to collect physiological data from users using one or more light-emitting components (e.g., light-emitting diodes (LEDs)) and one or more light-receiving components (e.g., photodiodes). Such physiological data may be used to assess various health-related parameters of the user, such as the user's heart rate, activity patterns, sleep quality, and the like. In some cases, LEDs of the wearable device may be connected to an electrical line (e.g., anode line) that may be charged to some voltage that enables the LEDs to perform physiological measurements.

BRIEF DESCRIPTION OF THE DRAWINGS

FIG. 6 shows a flowchart illustrating methods that support dynamic light emitting diode voltage control for wearable devices in accordance with aspects of the present disclosure.

DETAILED DESCRIPTION

Figure 1:
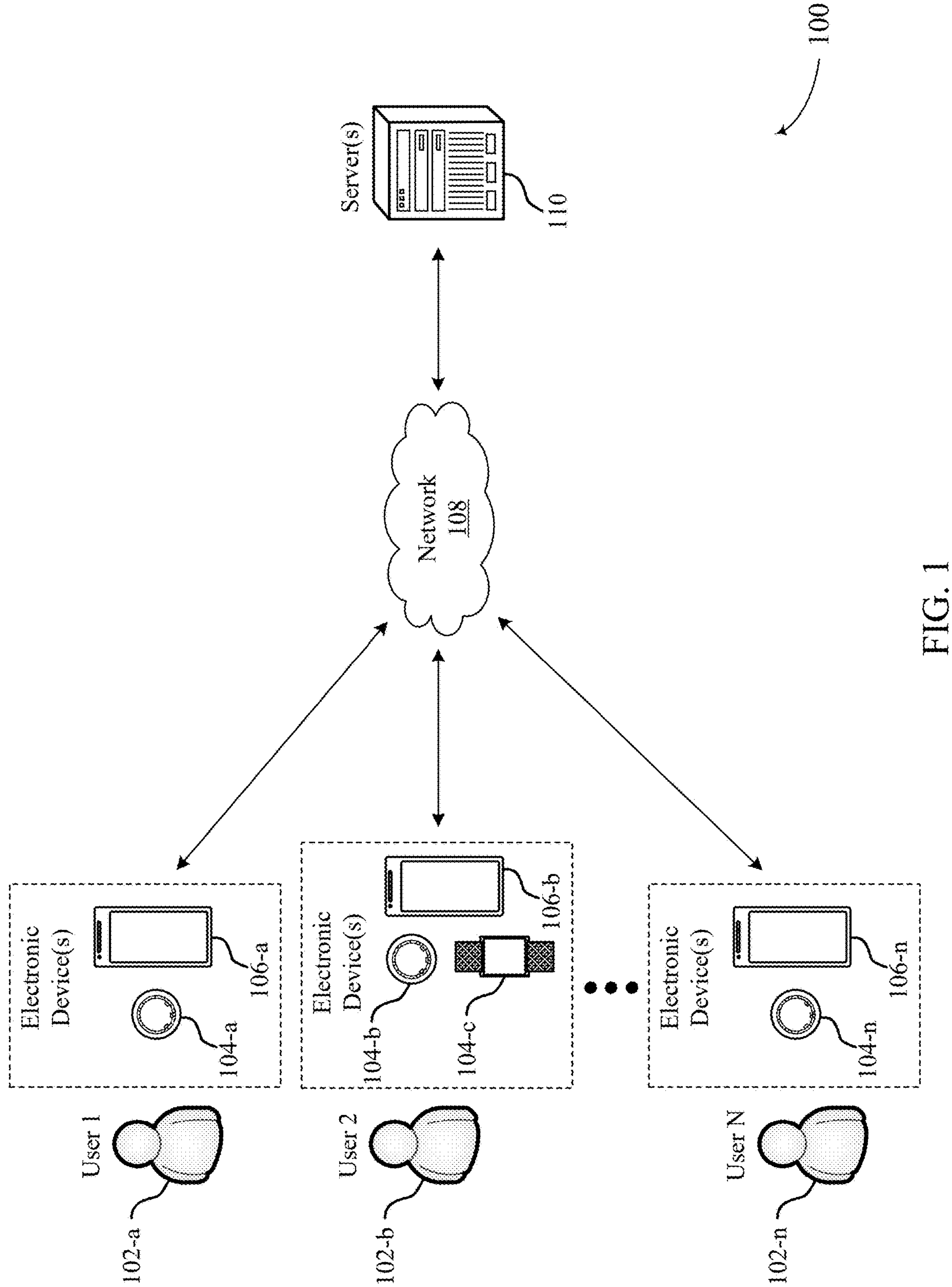
FIG. 1 illustrates an example of a system that supports dynamic light emitting diode (LED) voltage control for wearable devices in accordance with aspects of the present disclosure.

Wearable devices can be configured to collect physiological data from users to provide users with more information regarding their sleep patterns and overall health. Physiological data may be collected by emitting light from one or more light-emitting diodes (LEDs) of a wearable device, and measuring a reflected light signal via photodetectors. The LEDs of the wearable device may be coupled to a power supply (e.g., battery, converter(s)) via electronic circuitry including various electrical lines or traces, such as a power input line and an anode line. For example, the LEDs may be powered by one or more capacitors connected to the anode line, where the voltage of the anode line is controlled/adjusted via the voltage of the power input line. The LEDs may operate using a voltage (e.g., a minimum voltage to turn on). As such, before performing measurements using the LEDs, the anode line (e.g., capacitors of the anode line) may be charged to some "starting input voltage" (e.g., VLED) via the power input line. The voltage of the anode line (e.g., the capacitors) may decrease during intervals that the LEDs are activated to perform measurements, and may increase (e.g., "recharge") during intervals that the LEDs are inactive.

In a "fixed" VLED operation scheme, the starting input voltage of the LEDs prior to a measurement interval may be fixed (e.g., VLED=5V), regardless of a type of measurements to be performed. However, using a fixed VLED may result in the fixed VLED being higher than a minimum input voltage needed or expected to power the LEDs for some measurement intervals or certain types of measurements. That is, the wearable device may charge the anode line for longer durations between measurement intervals, which may increase latency in performing measurements via the wearable device. Further, using a higher VLED may result in components of the wearable device (e.g., LEDs, capacitors) aging relatively faster as compared to using a lower VLED, which may result in a relatively decreased quality of measurements and user experience.

Comparatively, in a "feature-based" VLED operation scheme, the starting input voltage of the LEDs may change based on the type of measurements to be performed. For instance, the starting input voltage may be set to 3.7V (VLED=3.7V) for standard photoplethysmogram (PPG) measurements, and may be set to 4.5V (VLED=4.5V) for daytime heart rate measurements. While such feature-based VLED operation may enable the VLED to be specific to a type of measurement, such techniques may not enable the wearable device to dynamically adjust how particular measurements are performed. For instance, if the wearable device increases the power of the LEDs to achieve higher quality daytime HR measurements, the starting VLED of 4.5V may not be sufficient to support the daytime HR measurements with increased LED power.

Accordingly, techniques described herein may enable a wearable device to dynamically select and adjust the starting input voltage (e.g., VLED) for the LEDs. In particular, a wearable device may utilize the "dynamic" VLED techniques described herein to dynamically determine the starting input voltage of the LEDs based on an LED configuration to be used by the LEDs, and a threshold anode line voltage to power the LEDs (e.g., a minimum voltage to power the LEDs for the respective LED configuration). The LED configuration may include parameters or characteristics of the LEDs to perform measurements, such as LED burn times, wavelength(s) to be used, LED pulse patterns, LED settling times, operating currents provided to the LEDs, etc. For example, the wearable device may determine an LED configuration that may be used to collect physiological data, and may perform simulations to model the voltage of the anode line throughout a measurement interval based on the LED configuration. Through the simulations, the wearable device may determine a starting input voltage of the anode line (e.g., VLED) that may maintain a voltage of the anode line above the threshold anode line voltage to power the LEDs throughout the measurement interval.

As such, techniques described herein may enable the wearable device to dynamically set the VLED voltage with increased granularity (e.g., on a per-LED configuration basis, rather than a per-feature basis). By performing dynamic LED voltage control as described herein, the wearable device may reduce power consumption and increase a quality of measurements and user experience by increasing a lifespan of the LEDs.

Aspects of the disclosure are initially described in the context of systems supporting physiological data collection from users via wearable devices. Aspects of the disclosure are further illustrated by and described with reference to circuit diagrams, voltage diagrams, block diagrams, apparatus diagrams, system diagrams, and flowcharts that relate to dynamic LED voltage control for wearable devices.

FIG. 1 illustrates an example of a system 100 that supports dynamic LED voltage control for wearable devices in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the car, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, blood oxygen saturation (SpO2), blood sugar levels (e.g., glucose metrics), and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-*a* (User 1) may operate, or may be associated with, a wearable device 104-*a* (e.g., ring 104-*a*) and a user device 106-*a* that may operate as described herein. In this example, the user device 106-*a* associated with user 102-*a* may process/store physiological parameters measured by the ring 104-*a*. Comparatively, a second user 102-*b* (User 2) may be associated with a ring 104-*b*, a watch wearable device 104-*c* (e.g., watch 104-*c*), and a user device 106-*b*, where the user device 106-*b* associated with user 102-*b* may process/store physiological parameters measured by the ring 104-*b* and/or the watch 104-*c*. Moreover, an nth user 102-*n* (User N) may be associated with an arrangement of electronic devices described herein (e.g., ring 104-*n*, user device 106-*n*). In some aspects, wearable devices 104 (e.g., rings 104, watches 104) and other electronic devices may be communicatively coupled to the user devices 106 of the respective users 102 via Bluetooth, Wi-Fi, and other wireless protocols. Moreover, in some cases, the wearable device 104 and the user device 106 may be included within (or make up) the same device. For example, in some cases, the wearable device 104 may be configured to execute an application associated with the wearable device 104, and may be configured to display data via a GUI.

In some implementations, the rings 104 (e.g., wearable devices 104) of the system 100 may be configured to collect physiological data from the respective users 102 based on arterial blood flow within the user's finger. In particular, a ring 104 may utilize one or more light-emitting components, such as LEDs (e.g., red LEDs, green LEDs) that emit light on the palm-side of a user's finger to collect physiological data based on arterial blood flow within the user's finger. In general, the terms light-emitting components, light-emitting elements, and like terms, may include, but are not limited to, LEDs, micro LEDs, mini LEDs, laser diodes (LDs) (e.g., vertical cavity surface-emitting lasers (VCSELs), and the like.

In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-*a* associated with the first user 102-*a* may be communicatively coupled to the user device 106-*a*, where the user device 106-*a* is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep, and classify periods of time that the user 102 is asleep into one or more sleep stages (e.g., sleep stage classification). For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time that the user 102-*a* is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g., in a hypothetical culture with 12 day "weeks," 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for a wearable device 104 to dynamically select and adjust a starting input voltage (e.g., VLED) for one or more LEDs. In particular, a wearable device 104 may utilize the dynamic VLED techniques described herein to dynamically determine the starting input voltage of the LEDs based on an LED configuration to be used by the LEDs, and a threshold anode line voltage to power the LEDs (e.g., a minimum voltage to power the LEDs for the respective LED configuration). The LED configuration may include parameters or characteristics of the LEDs to perform measurements, such as LED burn times, wavelength(s) to be used, LED pulse patterns, LED settling times, operating currents provided to the LEDs, etc. For example, the wearable device 104 may determine an LED configuration that may be used to collect physiological data, and may perform simulations to model the voltage of the anode line throughout a measurement interval based on the LED configuration. Through the simulations, the wearable device 104 may determine a value for VLED that may maintain a voltage of the anode line above the threshold anode line voltage to power the LEDs throughout the measurement interval.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
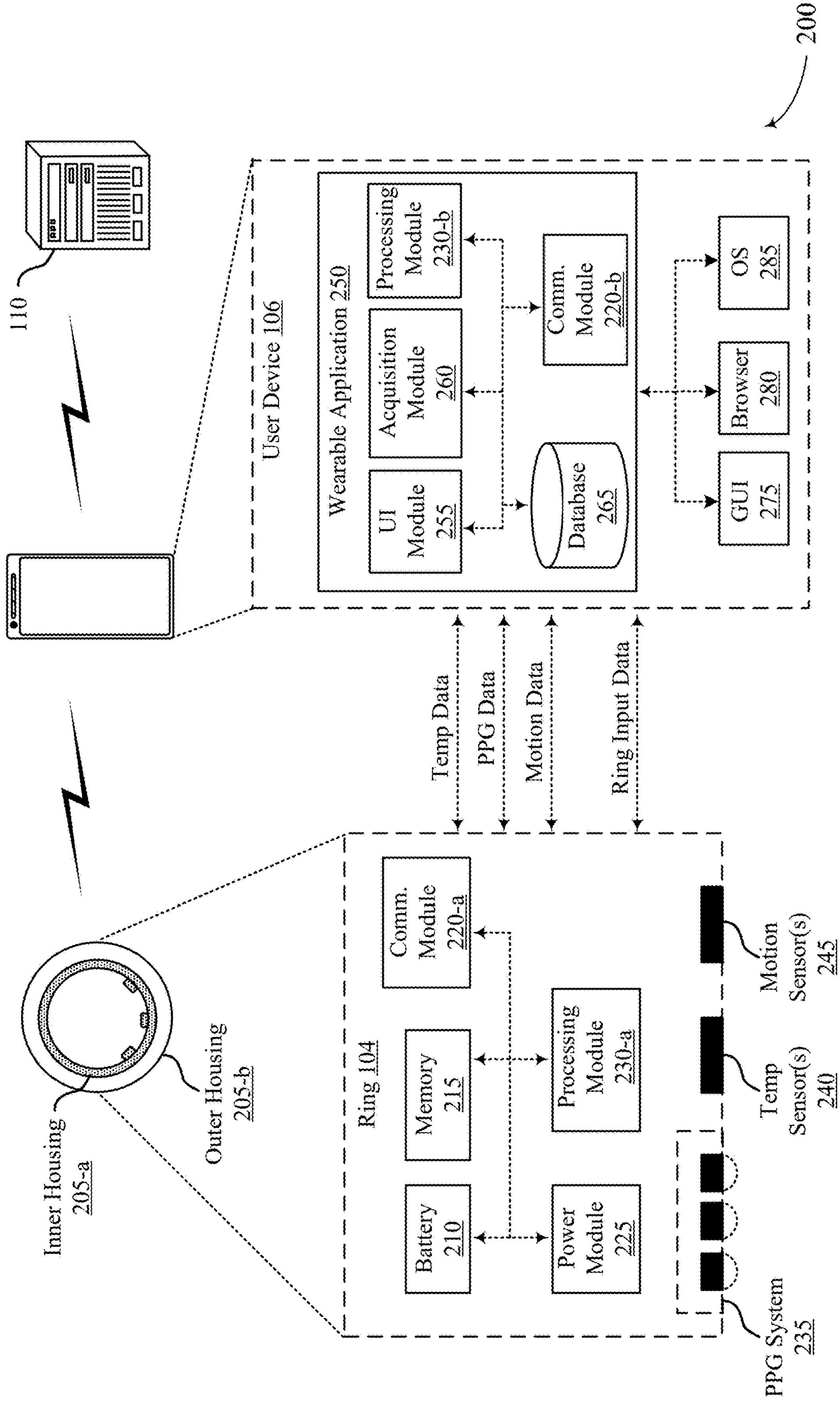
FIG. 2 illustrates an example of a system that supports dynamic LED voltage control for wearable devices in accordance with aspects of the present disclosure.

FIG. 2 illustrates an example of a system 200 that supports dynamic LED voltage control for wearable devices in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels (SpO2), blood sugar levels (e.g., glucose metrics), and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, PPG data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-*a* and an outer housing 205-*b*. In some aspects, the housing 205 of the ring 104 may store or otherwise include various components of the ring including, but not limited to, device electronics, a power source/supply (e.g., battery 210, converter, and/or capacitor), one or more substrates (e.g., printable circuit boards) that interconnect the device electronics and/or power source, and the like. The device electronics may include device modules (e.g., hardware/software), such as: a processing module 230-*a*, a memory 215, a communication module 220-*a*, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using adhesives, wraps, clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-*b* component (e.g., a shell) and an inner housing 205-*a* component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-*b* (e.g., a metal outer housing 205-*b*). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-*b* may be fabricated from one or more materials. In some implementations, the outer housing 205-*b* may include a metal, such as titanium, that may provide strength and abrasion resistance at a relatively light weight. The outer housing 205-*b* may also be fabricated from other materials, such polymers. In some implementations, the outer housing 205-*b* may be protective as well as decorative.

The inner housing 205-*a* may be configured to interface with the user's finger. The inner housing 205-*a* may be formed from a polymer (e.g., a medical grade polymer) or other material. In some implementations, the inner housing 205-*a* may be transparent. For example, the inner housing 205-*a* may be transparent to light emitted by the PPG LEDs. In some implementations, the inner housing 205-*a* component may be molded onto the outer housing 205-*b*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during charging, and under voltage during discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240. The processing module 230-*a* may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-*a* near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-*a* may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-*a* may sample the sensors at different rates and average/store different values for the different sensors. In some implementations, the processing module 230-*a* may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-*a* may sample the PPG signal and determine a user's pulse waveform based on the PPG signal. The processing module 230-*a* may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 where the optical receiver(s) receive transmitted light that is reflected through the region of the user's finger. In some implementations, the PPG system 235 may be configured as a transmissive PPG system 235 where the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-*a* may control one or both of the optical transmitters to transmit light while sampling the PPG signal generated by the optical receiver. In some implementations, the processing module 230-*a* may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-*a* may store the pulse waveform in memory 215 in some implementations. The processing module 230-*a* may process the pulse waveform as it is generated and/or from memory 215 to determine user physiological parameters described herein.

The processing module 230-*a* may determine the user's heart rate based on the pulse waveform. For example, the processing module 230-*a* may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBIs. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BM1160 inertial micro electro-mechanical system (MEMS) sensor that may measure angular rates and accelerations in three perpendicular axes.

The processing module 230-*a* may sample the motion signals at a sampling rate (e.g., 50 Hz) and determine the motion of the ring 104 based on the sampled motion signals. For example, the processing module 230-*a* may sample acceleration signals to determine acceleration of the ring 104. As another example, the processing module 230-*a* may sample a gyro signal to determine angular motion. In some implementations, the processing module 230-*a* may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-*a* may compress the data stored in memory 215. For example, the processing module 230-*a* may delete sampled data after making calculations based on the sampled data. As another example, the processing module 230-*a* may average data over longer periods of time in order to reduce the number of stored values. In a specific example, if average temperatures for a user over one minute are stored in memory 215, the processing module 230-*a* may calculate average temperatures over a five minute time period for storage, and then subsequently erase the one minute average temperature data. The processing module 230-*a* may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-*b*, a communication module 220-*b*, and a storage module (e.g., database 265) configured to store application data.

In some cases, the wearable device 104 and the user device 106 may be included within (or make up) the same device. For example, in some cases, the wearable device 104 may be configured to execute the wearable application 250, and may be configured to display data via the GUI 275.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

A wearable device (e.g., the ring 104) may have a relatively more limited power budget (e.g., battery capacity) than one or more other electronic devices due to a small form factor of the ring 104. The ring 104 may power or drive components of the ring 104 (e.g., LEDs of the PPG system 235) using a certain voltage (e.g., a minimum anode line voltage for the LEDs to produce light). That is, an amount of power consumed to drive each LED may depend on LED current and LED voltage (e.g., according to P=V*I). Accordingly, a lower LED voltage and/or a lower LED current may result in relatively less power consumption. However, if the LED voltage (e.g., anode line voltage) drops below a threshold (e.g., minimum) voltage, the LEDs may not produce light or may produce relatively less light than may be used to collect physiological data. To power the LEDs, in some examples, the ring 140 may use fixed or feature-based VLED operation schemes.

In a fixed VLED operation scheme, the starting input voltage of the LEDs prior to a measurement interval may be fixed (e.g., VLED=5V), regardless of an LED configuration or feature (e.g., a type of measurements to be performed). However, using a fixed VLED may result in the fixed VLED being higher than a minimum input voltage needed or expected to power the LEDs for some measurement intervals or certain types of measurements. That is, the ring 104 may charge the anode line for longer durations between measurement intervals, which may increase latency in performing measurements via the ring 104 and decrease a battery life of the ring 104. Further, higher VLED may result in LEDs aging relatively faster than lower VLED, which may result in a relatively decreased quality of measurements and user experience.

Comparatively, in feature-based VLED operation, the starting input voltage of the LEDs may change based on the type of measurements to be performed. For instance, the starting input voltage may be set to 3.7V (VLED=3.7V) for nighttime heart rate measurements, and may be set to 4.5V (VLED=4.5V) for daytime heart rate measurements. The ring 104 may use a fixed voltage (e.g., VLED=5.0) if multiple or conflicting features are enabled simultaneously (e.g., as a fallback VLED voltage). While such feature-based VLED operation may enable the VLED to be specific to a type of measurement, such techniques may not enable the wearable device to dynamically adjust how particular measurements are performed. For instance, if the wearable device increases the power of the LEDs to achieve higher quality daytime HR measurements, the starting VLED of 4.5V may not be sufficient to perform the daytime HR measurements with increased LED power.

In some aspects, the system 200 may support techniques for a wearable device (e.g., the ring 104) to dynamically select and adjust a starting input voltage (e.g., VLED) for one or more LEDs (e.g., the PPG LEDs in the PPG system 235). In particular, a wearable device may utilize the dynamic VLED techniques described herein to dynamically determine the starting input voltage of the LEDs based on an LED configuration to be used by the LEDs, and a threshold anode line voltage to power the LEDs (e.g., a minimum voltage to power the LEDs for the respective LED configuration). The LED configuration may include parameters or characteristics of the LEDs to perform measurements, such as LED burn times, wavelength(s) to be used, LED pulse patterns, LED settling times, operating currents provided to the LEDs, etc.

For example, the wearable device (e.g., ring 104) may determine an LED configuration (e.g., a configuration stored in the memory 215 or indicated to the ring 104 by the user device 106) that may be used to collect physiological data. The wearable device may perform simulations (e.g., an electronics transient simulation) to model the voltage of the anode line throughout a measurement interval based on the LED configuration (e.g., via the processing module 230-*a*). Through the simulations, the wearable device 104 may determine a value for VLED that may maintain a voltage of the anode line above the threshold anode line voltage to power the LEDs throughout the measurement interval. Additionally, or alternatively, the wearable device may perform one or more calculations via the processing module 230-*a* to determine the value for VLED. The wearable device may apply the value for VLED to perform one or more measurements via the PPG system 235 during a measurement interval according to the LED configuration.

Figure 3:
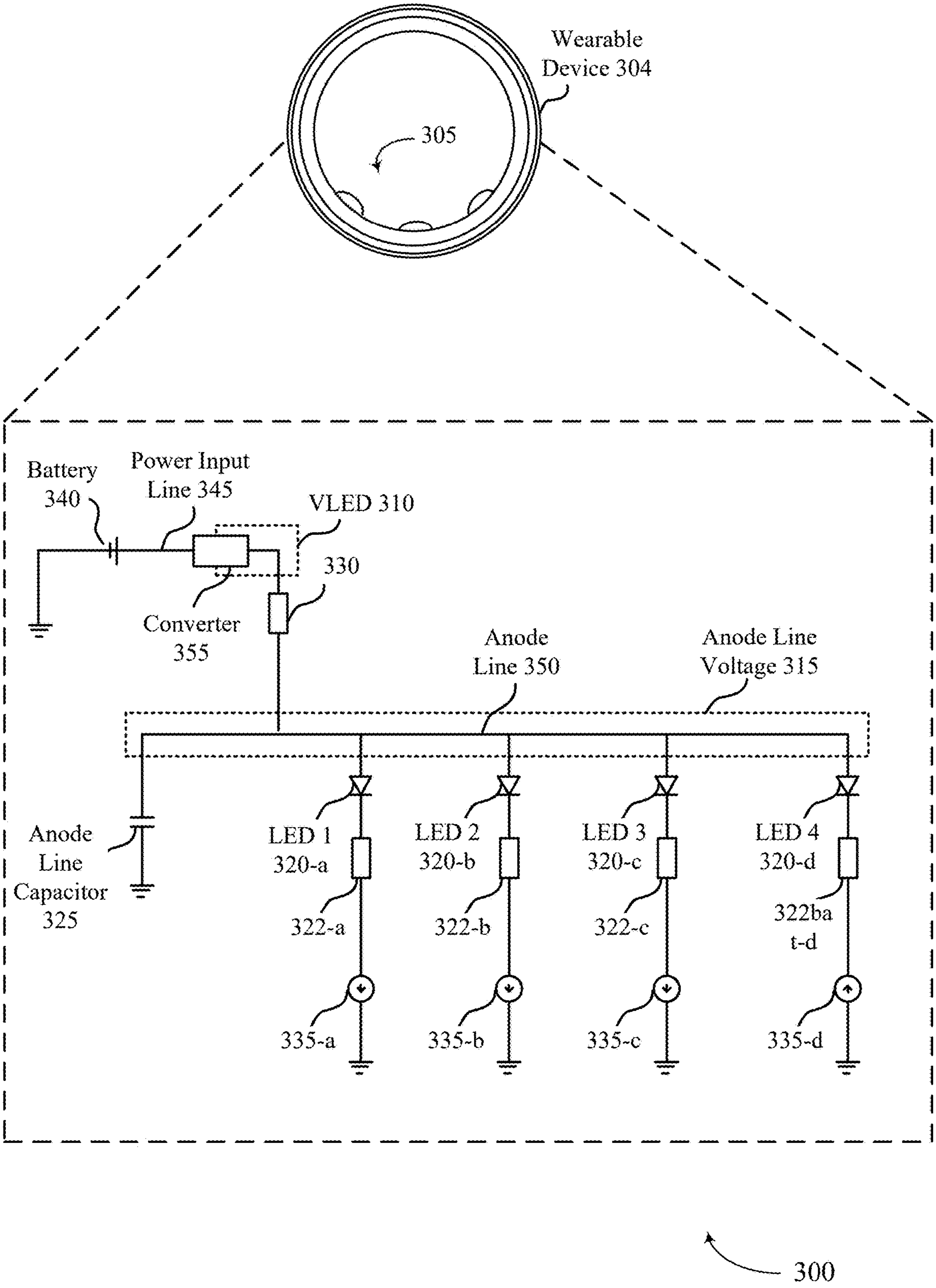
FIG. 3 shows an example of a circuit diagram that supports dynamic LED voltage control for wearable devices in accordance with aspects of the present disclosure.

FIG. 3 shows an example of a circuit diagram 300 that supports dynamic LED voltage control for wearable devices in accordance with aspects of the present disclosure. The circuit diagram 300 may implement, or may be implemented by, aspects of the system 100 and the system 200. For example, the circuit diagram 300 may be used by a wearable device 304, which may be an example of a wearable device 104 as described with reference to FIG. 1.

A wearable device 304 (e.g., a wearable ring device, a wrist-worn wearable device) may power one or more LEDs 320 (e.g., light-emitting components) of a PPG measurement system 305 according to the circuit diagram 300. As noted previously herein, the PPG measurement system 305 may include one or more light-emitting components (e.g., LEDs 320) and one or more light-receiving components (e.g., photodiodes, phototransistors). As shown in FIG. 3, the light-emitting and/or light-receiving components of the PPG measurement system 305 may be at least partially disposed within "domes" or other structures extending from the inner circumferential surface of the wearable device 304. The LEDs 320 (e.g., LEDs 320-*a*, 320-*b*, 320-*c*, 320-*d*) may include any quantity of LEDs, any model or combination of models of LEDs, and may emit light of any wavelength or combination of wavelengths (e.g., red, infrared, green, and so on). For example, the first LED 320-*a* may be configured to emit red light, the second and third LEDs 320-*b*, 320-*c* may be configured to emit green light, and the fourth LED 320-*d* may be configured to emit IR light. The wearable device 304 may collect physiological data associated with a user by measuring light emitted from the LEDs 320 via one or more light-receiving components (e.g., photodiodes, phototransistors).

The wearable device 304 may use a power supply, such as a battery 340 and/or one or more converter(s) 355 (e.g., a switching power supply, such as a buck-boost converter) to generate a starting input voltage, which may be referred to as VLED 310, that may be used to charge the anode line 350. That is, the one or more converters 355 may receive the voltage output from the battery 340 and convert the battery voltage to charge the anode line to VLED 310 for powering the LEDs 320. As will be described in further detail herein, the starting input voltage/VLED 310 voltage output by the converter 355 may be calculated via electronics simulations. Moreover, for the purposes of the present disclosure, the battery 340 and/or the converter(s) 355 (e.g., buck-boost converter) may be used and/or referred to as a "power supply," "power supply components," or like terms.

The wearable device 304 may accordingly power/charge an anode line 350 to the input voltage VLED 310 by charging one or more anode line capacitors 325 to the input voltage VLED 310. An anode line voltage 315 may increase (e.g., to VLED 310) as the anode line capacitors 325 charge, and may decrease as the anode line capacitors 325 discharge (e.g., to power the LEDs 320). The wearable device 304 may control (e.g., limit) a current between the power input line 345 and the anode line 350 via a resistor 330 (e.g., to prevent large current spikes on the battery 340) and/or one or more converters 355. For example, the wearable device 304 may include one or more converters (e.g., buck-boost converters) disposed on the power input line 345 between the battery 340 and the resistor 330.

The anode line capacitors 325 may provide energy storage for short-duration LED current pulses provided to the LEDs 320 to perform physiological measurements. For example, the anode line capacitors 325 may charge the anode line 350 to an anode line voltage 315 to power an LED 320-*a*, and LED 320-*b*, an LED 320-*c*, and/or an LED 320-*d*. The anode line capacitors 325 may discharge to power the LEDs 320 and may recharge between LED pulse bursts (e.g., frames during which the LEDs 320 are inactive). The anode line capacitors 325 may include any quantity of capacitors, any material of capacitor, any model of capacitors, and so on. The wearable device 304 may use a model of the anode line capacitors 325 (e.g., and one or more other components of the circuit diagram 300 described herein) to perform VLED estimation.

The wearable device 304 may control a drive current and/or voltage for each LED 320 using a corresponding analog front-end (AFE) LED driver 335 (e.g., an AFE LED driver 335-*a*, an AFE LED driver 335-*b*, an AFE LED driver 335-*c*, and an AFE LED driver 335-*d*). The wearable device 304 may include any quantity of AFE LED drivers 335 and any model or combination of models of AFE LED drivers 335. Each AFE LED driver 335 may have different parameters (e.g., timing parameters, LED drive current/voltage limitations, tolerances, and so on). The wearable device 304 may use a model of each AFE LED driver 335 (e.g., and one or more other components of the circuit diagram 300 described herein) to perform VLED estimation. Each AFE LED driver 335-*c* may be an example of an AFE chip and may operate the corresponding LED using a waveform (e.g., a pulse pattern). In some aspects, the AFE LED driver(s) 355 may be configured or otherwise set up with specific currents for respective LED configurations, where the respective (e.g., constant) currents are used for powering LED pulses in accordance with the respective LED configurations.

The wearable device 304 may control a drive current and/or voltage through each LED 320 using a corresponding resistor 322 (e.g., a resistor 322-*b*, a resistor 322-*c*, a resistor 322-*d*, and a resistor 322-*e*). In some implementations, the corresponding resistors 322 may include one or more components (e.g., AFE components) to control a current through the LEDs 320. That is, the resistors 322 may include current sinks that may function as adjustable resistors to control the drive current. In some other implementations, the wearable device 304 may not include the resistors 322, or the resistors 322 may be implemented within the AFE LED drivers 335. Accordingly, the wearable device may cause the LEDs 320 to emit light (e.g., pulse) according to an LED configuration. In some examples, to power the LEDs 320 with a larger drive current, the wearable device 304 may also power the LEDs 320 with a larger voltage. Different models of LEDs 320 may have different characteristics (e.g., minimum voltages, forward voltages at different currents, voltage tolerances, relations between drive current and drive voltage, and so on). The wearable device 304 may use a model of each LED 320 (e.g., and one or more other components of the circuit diagram 300 described herein) to perform VLED estimation. The LEDs 320 and corresponding resistors 330 and AFE LED drivers 335 may be connected to the anode line 350 in parallel.

As described herein, an LED configuration may define which LEDs 320 (e.g., associated with given wavelengths) are powered (e.g., driven) during each slot of a measurement interval, as well as one or more LED parameters such as LED current, LED drive current/voltage, measurement patterns of LED pulses, idle time between LED pulses, a quantity of LED pulses, and the like. As an illustrative example, an LED configuration may enable the wearable device 304 to power the LED 320-*a* (e.g., a red LED 320-*a*) using a first voltage and current for a first duration (e.g., a pulsing instance), to leave the LEDs 320 inactive for a second duration (e.g., a settling period), to power the LED 320-*b* (e.g., a green LED) using a second voltage and current for a third duration (e.g., a pulsing instance), and so on. In this regard, the term "LED configuration" may be used to refer to a set of parameters or characteristics of the LEDs 320 and/or other components of the wearable device 304 that are used to perform physiological measurements for some measurement interval.

In some examples, to power the LEDs 320, the wearable device 304 may power the anode line 350 to at least a minimum anode line voltage for a duration of a measurement period (e.g., a duration defined by an LED configuration). The minimum anode line voltage may be a minimum voltage that may enable the LEDs 320 to operate throughout a measurement interval according to an LED configuration. For example, if the anode line voltage 315 is below the minimum anode line voltage, one or more of the LEDs 320 may be inactive or may have a brightness that is below a threshold that is expected or otherwise used to perform physiological measurements with sufficiently high quality. In other words, if the anode line voltage 315 is below the minimum anode line voltage, the LEDs 320 may not fire, or physiological data collected using the LEDs 320 may exhibit poor quality.

In some examples, the wearable device 304 may determine the minimum anode line voltage by performing one or more physiological measurements using the LEDs 320 (e.g., at a first anode line voltage 315) and the light-receiving components. The wearable device 304 may determine if a measurement quality (e.g., a received power) of the physiological measurements is above a threshold. If the measurement quality is below the threshold, the wearable device 304 may determine that the first anode line voltage 315 is below the minimum anode line voltage. In some examples, the minimum anode line voltage may be an overall minimum anode line voltage, an LED-specific minimum anode line voltage, or a slot-specific or LED configuration-specific minimum anode line voltage (e.g., specific to an LED configuration). For example, a first LED configuration (e.g., first set of parameters/characteristics used to acquire physiological data) may be associated with a first minimum anode line voltage, and a second LED configuration may be associated with a second minimum anode line voltage.

The wearable device 304 may dynamically calculate (e.g., determine, select) the starting input voltage (e.g., VLED 310) based on an LED configuration that is to be used and the corresponding minimum anode line voltage for the LED configuration. For example, the wearable device 304 may dynamically calculate VLED 310 such that the wearable device 304 may maintain a measurement quality (e.g., received power) associated with physiological measurements performed using the LEDs 320 above the threshold measurement quality throughout a measurement interval using the LED configuration. That is, the wearable device 304 may dynamically calculate VLED 310 to maintain the anode line voltage 315 above the minimum anode line voltage throughout the measurement interval.

In some examples, the wearable device 304 may calculate a VLED 310 for each LED configuration by performing a forwards simulation of the anode line voltage 315 with a respective LED configuration or by performing a backwards simulation of the anode line voltage 315 with the respective LED configuration, as described with reference to FIG. 4. The wearable device 304 may accordingly separately calculate a VLED corresponding to each LED configuration, which may increase a measurement quality and battery life of the wearable device 304.

To summarize, the wearable device 304 (e.g., processors of the wearable device 304) may determine an LED configuration that will be usable by the LEDs 320 to perform physiological measurements throughout a measurement interval. The wearable device 304 may then determine a minimum voltage of the anode line 350 that will be “required” (e.g., expected, used) to perform the measurements throughout the measurement interval based on the selected LED configuration. The wearable device 304 may then perform simulations or may otherwise calculate a starting input voltage (VLED 310) of the anode line 350 that will not cause the anode line voltage 315 to drop below the minimum anode line voltage throughout the measurement interval. Subsequently, prior to the measurement interval, the wearable device 304 may utilize the power supply (e.g., battery 340 and/or converter(s) 355) to charge the power input line 345 and/or anode line 350 to VLED 310, and may subsequently perform measurements during the measurement interval using the LEDs 320. As such, by calculating and charging the power input line 345 and/or anode line 350 to VLED 310, the “dynamic” VLED techniques described herein may be used to ensure that the anode line voltage 315 does not drop below the minimum anode line voltage usable for the LEDs 320 to perform measurements with sufficiently high quality using the LED configuration throughout the measurement interval.

Techniques described herein may enable the wearable device to charge the anode line 350 to the minimum VLED 310 that will enable physiological measurements throughout the measurement interval 301. As such, techniques described herein may enable the wearable device to tailor the VLED 310 for each measurement interval 301 to the LED configuration that will be used. For example, instead of always charging the anode line 350 to a static VLED (e.g., static VLED=5V) in accordance with a “fixed” VLED configuration, the “dynamic” VLED techniques described herein may enable the wearable device to instead tailor the VLED to the specific LED configuration to be used (e.g., charge to only 3.7V for some LED configurations). As such, the dynamic VLED techniques described herein may reduce the amount of time between measurement intervals 301 by dynamically adjusting the VLED 310 to be used, thereby reducing latency between measurement intervals 301 and corresponding physiological measurements.

Figure 4:
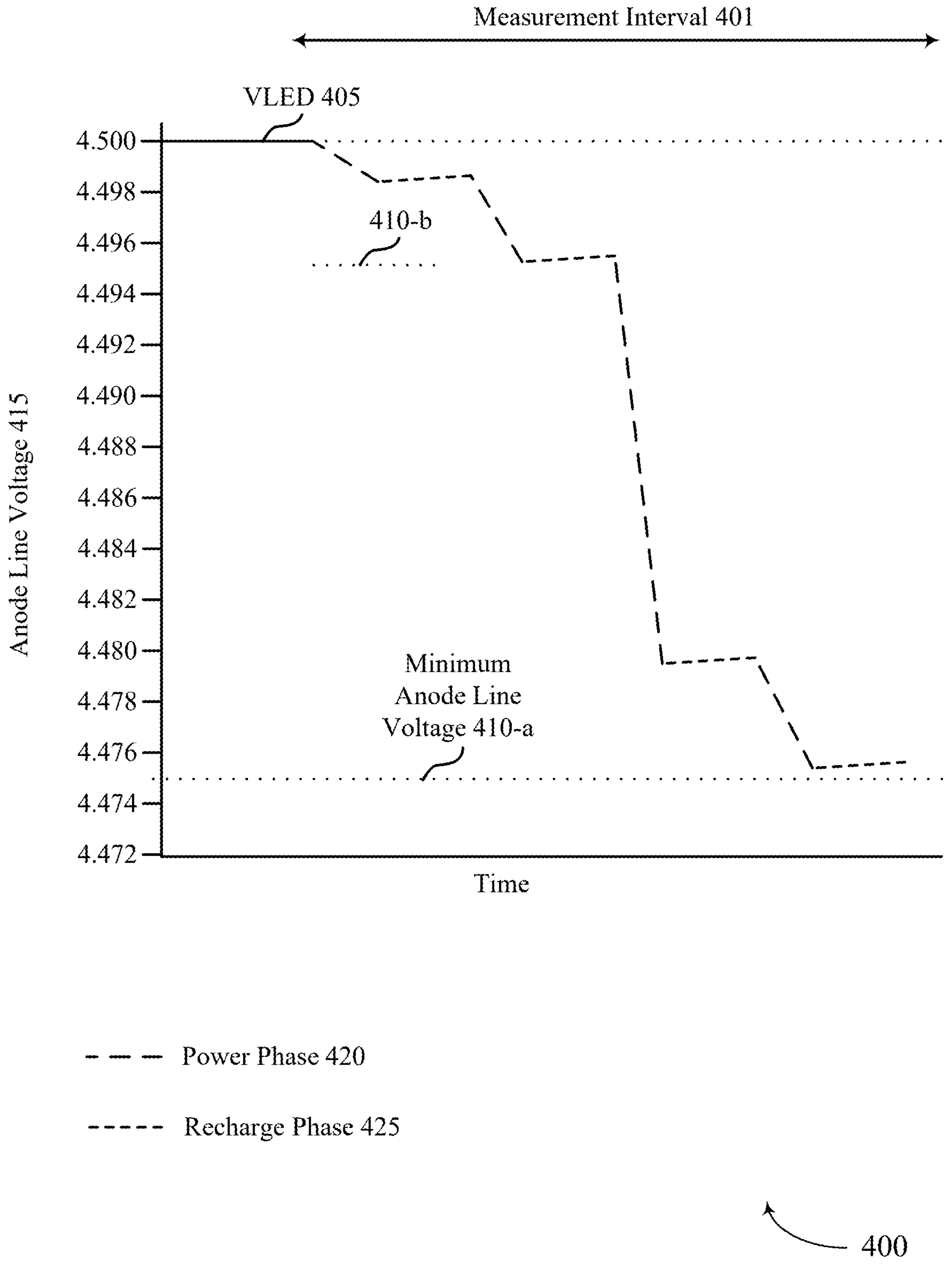
FIG. 4 shows an example of a voltage diagram that supports dynamic LED voltage control for wearable devices in accordance with aspects of the present disclosure.

FIG. 4 shows an example of a voltage diagram 400 that supports dynamic LED voltage control for wearable devices in accordance with aspects of the present disclosure. The voltage diagram 400 may implement, or may be implemented by, aspects of the system 100, the system 200, or the circuit diagram 300. For example, the voltage diagram 400 may be used by a wearable device, which may be an example of a wearable device 104 as described with reference to FIG. 1.

The voltage diagram 400 may be an illustrative example of an anode line voltage 415 over a measurement interval 401 that includes a set of PPG slots (e.g., power phases 420 during which the LEDs are powered and an anode line capacitor is discharging) and recharge phases 425 (e.g., during which the LEDs are inactive or not powered and the anode line capacitor is recharging). As shown in FIG. 4, the anode line voltage 415 may decrease during the power phases 420 during which the LEDs are firing (e.g., emitting light for measurements), and may increase during the recharge phases 425 of the measurement interval 401 during which the LEDs are inactive. In other words, the anode line capacitors 325 (and therefore the anode line voltage 415) may be discharged during the power phases 420 of the measurement interval 401, and may be recharged during the recharge phases 425 of the measurement interval 401. In some aspects, the wearable device 304 (e.g., a wearable ring device, a wrist-worn wearable device) may charge the anode line voltage 415 to a starting input voltage VLED 405 at a start of the measurement interval 401.

As described herein, an LED configuration may define which LEDs (e.g., associated with given wavelengths) are powered (e.g., driven) during each slot of a measurement interval 401, as well as one or more LED parameters such as LED current, LED drive current/voltage, measurement patterns of LED pulses, idle time between LED pulses, a quantity of LED pulses, and the like. The voltage diagram 400 may be an illustrative example of the anode line voltage 415 during a measurement interval 401 according to an example LED configuration. As described herein, a power phase 420 may be a pulsing instance of a measurement interval 401 and a recharge phase 425 may be a settling period of the measurement interval 401.

In some aspects, as described with reference to FIG. 3, each LED configuration may be associated with a minimum anode line voltage 410-*a* that is used (e.g., expected, required) to power the LEDs throughout the measurement interval 401. In other words, the anode line voltage 415 must be maintained at or above the minimum anode line voltage 410-*a* for the duration of the measurement interval 401 in order for the LEDs to be able to perform sufficiently high quality measurements throughout the measurement interval 401. Similarly, the LED configuration may be associated with one or more minimum slot-specific anode line voltage 410-*b* for a given LED configuration used during a pulsing instance (e.g., a slot) of a first PPG slot (e.g., and one or more additional minimum slot-specific anode line voltages corresponding to each additional PPG slot). The minimum slot-specific anode line voltages 410-*b* may indicate or represent intermediate voltages that must be maintained at various points/slots throughout the measurement interval 401 to enable the LEDs to perform measurements throughout the measurement interval 401.

In this regard, the wearable device may determine an LED configuration that is to be used to perform measurements during a respective measurement interval 401, and may determine/calculate the minimum anode line voltage 410-*a* for the LED configuration/measurement interval 401. Subsequently, the wearable device may select/calculate a VLED 405 such that the anode line voltage 415 does not fall below the minimum anode line voltage 410-*a* at any point during a measurement interval 401, and such that the anode line voltage 415 does not fall below the minimum slot-specific anode line voltage 410-*b* during a corresponding slot (e.g., the first slot) of the measurement interval 401. A minimum slot-specific anode line voltage 410-*b* of a given PPG slot (e.g., power phase 420) may be LED-specific or LED configuration-specific based on an LED model, LED drive current, AFE settings, and the like for the given PPG slot.

In some examples, the wearable device may calculate the VLED 405 by performing a forward simulation corresponding to the LED configuration. For example, the wearable device may set an anode line voltage 415 to an estimated VLED 405, and may simulate the anode line voltage 415 during one or more slots of a measurement interval (e.g., during one or more voltage increases corresponding to recharge phases 425 and during one or more voltage decreases corresponding to the power phases 420). If the anode line voltage 415 falls below the minimum anode line voltage 410-*a* at any point during the measurement interval 401 (e.g., or falls below a minimum slot-specific anode line voltage 410-*b* during a corresponding slot), the wearable device may restart the simulation using a relatively higher VLED 405 (e.g., higher by a configured amount). Conversely, if the anode line voltage 415 does not fall below the minimum anode line voltage 410-*a* at any point during the measurement interval 401 (e.g., or does not fall below a minimum slot-specific anode line voltage 410-*b* during a corresponding slot), the wearable device may restart the simulation using a relatively lower VLED 405 (e.g., lower by a configured amount). In such cases, the wearable device may perform simulations in a trial-and-error manner by starting with different VLEDs 405, and calculating the lowest anode line voltage 415, and comparing the lowest anode line voltage 415 to the minimum anode line voltage 410-*a* to identify the minimum VLED 405 (e.g., minimum starting input voltage) that will maintain the anode line voltage 415 at or above the minimum anode line voltage 410-*a* for the duration of the measurement interval 401.

The wearable device may perform a threshold quantity of simulations, or may repeat the simulation until a first simulation indicates for the wearable device to increase the VLED 405 and a subsequent simulation indicates for the wearable device to decrease the VLED 405 (e.g., or vise-versa). The wearable device may use the higher VLED 405 to power the LEDs for the LED configuration used to perform the simulation.

Additionally, or alternatively, the wearable device may calculate the VLED 405 by performing a backwards simulation. For example, the wearable device may determine a point in time in the LED configuration at which the anode line voltage 415 is at a lowest point. The wearable device may accordingly set the anode line voltage 415 at the point in time corresponding to the lowest point to the minimum anode line voltage 410-*a* (e.g., or to a minimum slot-specific anode line voltage 410-*b* corresponding to the slot containing the point in time if the minimum slot-specific anode line voltage 410-*b* is higher than the minimum anode line voltage 410-*a*) and may run a backwards simulation starting from the point in time and moving to an initial time. That is, the wearable device may simulate the anode line voltage 415 moving backwards in time in the LED configuration by starting with the known minimum anode line voltage 410-*a* and backwards-calculating the VLED 405.

At each slot (e.g., each local minimum, as illustrated with reference to the voltage diagram 400), the wearable device may set the anode line voltage 415 to a voltage calculated thus far in the backwards simulation, or to a minimum slot-specific anode line voltage 410-*b* corresponding to the given slot (e.g., if the minimum slot-specific anode line voltage 410-*b* is higher than the voltage calculated thus far). The wearable device may determine that a starting voltage (e.g., a final voltage calculated representing a starting voltage of the simulation at the initial time) may be the VLED 405. The wearable device may use the VLED 405 to power the LEDs for the LED configuration used to perform the simulation.

In other words, after calculating/identifying VLED 405 for the LED configuration/measurement interval 401, the wearable device may charge the anode line 350 to VLED 405 (e.g., anode line voltage 415=VLED 405) prior to a start of the measurement interval 401. As such, the VLED 405 may enable the LEDs of the wearable devices to perform measurements (that satisfy a quality threshold) throughout the measurement interval 401.

The wearable device may perform the forward simulation and/or the backwards simulation using a model of the anode line voltage 415 based on one or more circuit components (e.g., the LEDs 320, the anode line capacitors 325, one or more AFE LED drivers 35, one or more resistors 330, 322, a battery 340, and the like as described with reference to FIG. 3). Equation 1 provides an example model for the anode line voltage 415 at a time $t_{n+1}$ that is Δt=1 microsecond after a time $t_n$ (e.g., $V_{CommonAnode}(t_{n+1})$) during a power phase 420:

$$V_{CommonAnode}(t_{n+1}) = \frac{V_{LED} * R_{R1} + V_{C1}(t_n) * R_{R1} - I_{AFE} * R_{R1} * R_{C1}}{R_{R1} + R_{C1}} \qquad (1)$$

As described with reference to Equation 1, $R_{C1}$ may be a resistance of the anode line capacitors 325 defined as $$R_{C1} = \frac{\Delta t}{C_{C1}}$$

where $L_{C1}$ is a capacitance of the anode line capacitors 325, $I_{AFE}$ may be a current through an AFE corresponding to an LED 320 (e.g., a sum of a current provided by the anode line capacitors $I_{C1}$ and a current provided via the power input line 345 $I_{VLED}$), $V_{C1}$ may be a voltage of the anode line capacitors 325, and $R_{R1}$ may be a resistance of a resistor 330 between the power input line 345 and the anode line 350. During a recharge phase 425, the AFE current may be $I_{AFE}$=0.

The wearable device may perform the forward simulation and/or the backward simulation using each LED configuration used by the wearable device (e.g., to determine a respective VLED 405 for each respective LED configuration). The wearable device may perform the forward simulation using a predefined range of acceptable voltages (e.g., between 3.3V and 5.0V) using either linear search or binary search. Accordingly, the wearable device may calculate a lowest VLED 405 for which the anode line voltage 415 does not fall below any acceptable criteria (e.g., the minimum anode line voltage 410-*a* or a minimum slot-specific anode line voltage 410-*b* of a corresponding slot) during the simulation across the measurement interval 401.

In some aspects, if a wearable device does not have a configurable or dynamic VLED 405 (e.g., the wearable device has an anode line or LEDs connected to a battery voltage (VBAT), the wearable device may use a simulation as described herein to determine a validity (e.g., possibility)

of PPG or LED configurations (e.g., to prevent use of non-valid configurations that may not be used with hardware supported by the wearable device). Additionally, or alternatively, the wearable device may use a simulation as described herein to select or limit LED drive currents (e.g., to a maximum LED drive current supported by the battery).

Figure 5:
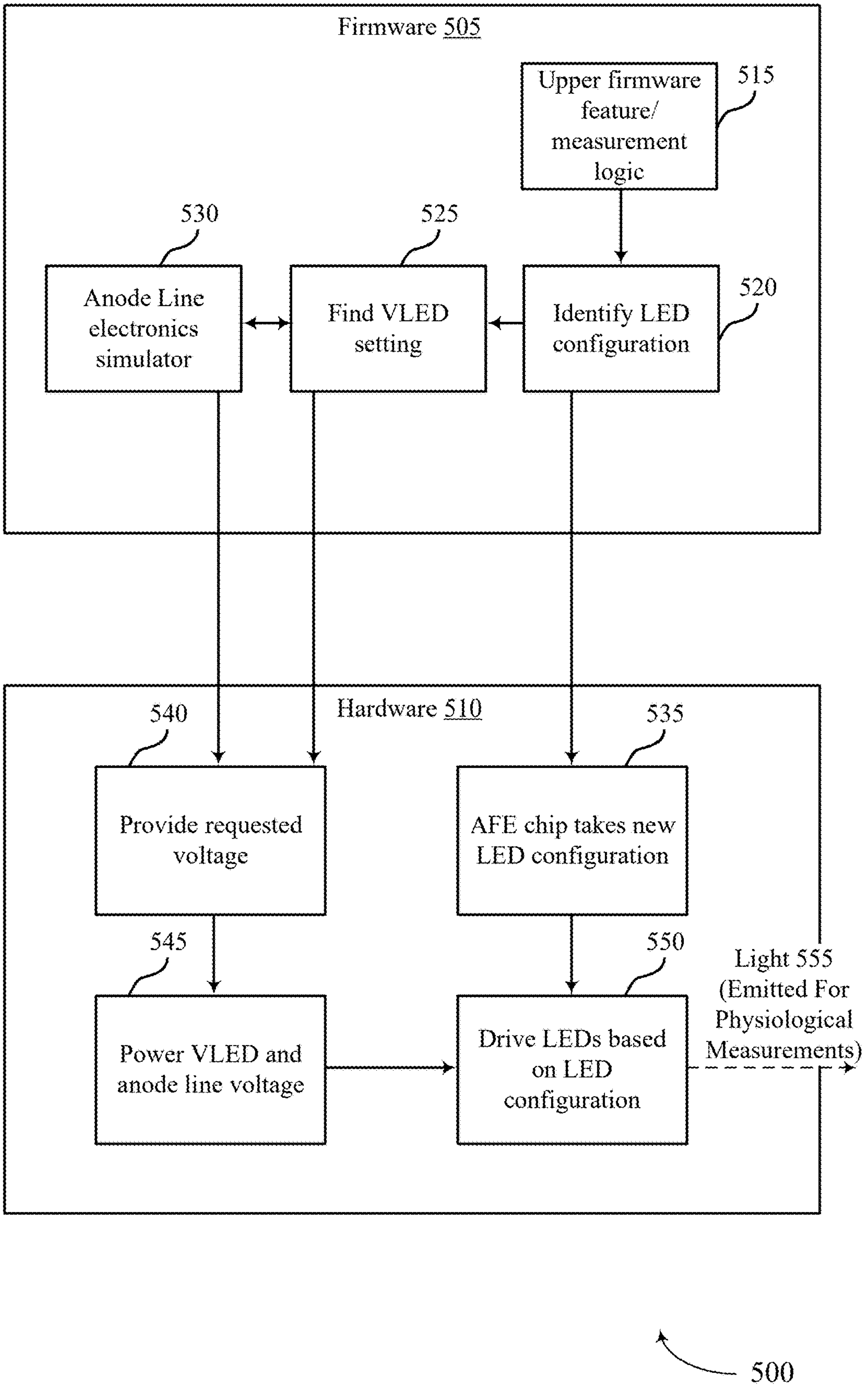
FIG. 5 shows an example of a block diagram that supports dynamic LED voltage control for wearable devices in accordance with aspects of the present disclosure.

FIG. 5 shows an example of a block diagram 500 that supports dynamic LED voltage control for wearable devices in accordance with aspects of the present disclosure. The block diagram 500 may implement, or may be implemented by, aspects of the system 100, the system 200, the circuit diagram 300, or the voltage diagram 400. For example, block diagram 500 may illustrate or be used by a wearable device, such as a wearable device 104 (e.g., a wearable ring device, a wrist-worn wearable device) as described with reference to FIG. 1.

A wearable device (e.g., a wearable ring device, a wrist-worn wearable device) may include firmware 505 and hardware 510. The firmware 505 may be operable by one or more processors and may include components capable of identifying or configuring light-emitting configurations (e.g., LED configurations, as described herein), simulating electronic/hardware components, as described with reference to FIG. 4, and/or dynamically determining an LED input voltage VLED corresponding to each LED configuration. The hardware 510 may include sensors such as light-emitting components (e.g., LEDs) and light-receiving components (e.g., photodiodes, phototransistors) capable of emitting and measuring light pulses to collect physiological data, one or more AFE components (e.g., on an AFE chip) capable of operating the light-emitting components and the light-receiving components according to the LED configurations, one or more components (e.g., batteries, capacitors, resistors, converters, and the like) capable of providing power (e.g., the input voltage VLED) to the sensors of the wearable device, electronic circuitry (e.g., an anode line and a power input line) coupling the power-providing components to the sensor components, and so on as described with reference to FIG. 3.

At 515, the wearable device may use one or more components of the firmware 505 (e.g., upper firmware feature/measurement logic components) to determine one or more LED settings. For example, the wearable device may determine to perform a measurement of physiological data of a user (e.g., a feature) during a measurement interval.

At 520, the wearable device may provide LED settings (e.g., the minimum anode line voltages) and a selected feature to an LED configuration component to identify an LED configuration for the selected feature. The LED configuration may be a configuration for operating the light-emitting components (e.g., the LEDs), such as a device voltage for one or more pulse instances, a drive current for one or more pulse instances, a current provided to the LEDs during each pulse instance of a measurement interval, a duration of the measurement interval, a measurement pattern for the measurement interval (e.g., including timing and/or durations such as burn times of pulse instances and settling periods, as described with reference to FIG. 4), an indication of which LEDs are to be active at each point in the measurement pattern, one or more wavelengths of light used by the one or more LEDs during the measurement interval, and so on. The wearable device may identify the LED configuration based on a signal measured while performing the physiological measurements.

The wearable device may determine one or more minimum anode line voltages of the anode line to power the LEDs to perform the measurement. In particular, the wearable device may determine the minimum anode line voltage 410-*a* for the LED configuration that is to be used to perform measurements throughout the measurement interval 401. In some examples, the one or more minimum anode line voltages may be an overall minimum anode line voltage or a set of minimum anode line voltages each corresponding to a pulsing instance (e.g., a power phase) of one or more LEDs according to an LED configuration.

At 525, the wearable device may perform one or more calculations to calculate a starting input voltage VLED of the power input line (e.g., to input to the anode line) based on the one or more minimum anode line voltages corresponding to the LED configuration. In some examples, at 530, the wearable device may use a model of the anode line voltage to perform one or more simulations of a measurement interval to calculate the starting input voltage VLED (e.g., based on one or more resistances, capacitances, currents, and voltages, as described with reference to FIGS. 3 and 4). The one or more simulations may be forward simulations (e.g., to determine if a given VLED may maintain an anode line voltage above the one or more minimum anode line voltages) or backwards simulations (e.g., to identify a VLED based on a lowest anode line voltage associated with the corresponding LED configuration). The simulations may include simulating one or more voltage decreases in the anode line voltage during one or more pulsing instances of the measurement pattern and simulating one or more voltage increases of the anode line voltage during one or more settling periods of the measurement pattern.

In some examples, the firmware 505 of the wearable device may perform the operations 515, 520, 525, and 530 one or more times to identify a set of LED configurations for one or more features and a corresponding input voltage VLED for each of the set of LED configurations. In some examples, each respective LED configuration may have a different charging duration (e.g., a duration taken for the wearable device to charge the anode line to the input voltage VLED prior to performing measurements according to the respective LED configuration) corresponding to each respective VLED. For example, an LED configuration with a relatively larger VLED may have a longer charging duration than an LED configuration with a relatively smaller VLED.

At 535, the firmware 505 may indicate for a component of the hardware 510 (e.g., the AFE component) to operate the LEDs according to the LED configuration. At 540, the firmware 505 may instruct the power-providing components (e.g., the battery, the converter) to charge the power input line (e.g., and accordingly the anode line and one or more capacitors of the anode line) to the determined input voltage VLED. For example, the power-providing components (e.g., power supply, including the battery, converters, etc.) may charge the power input line to the input voltage VLED during a corresponding charging duration (e.g., a charging duration between a previous measurement interval and the measurement interval). Charging the power input line to the determined input voltage VLED may result in charging one or more capacitors coupled with the anode line (e.g., to VLED). Accordingly, at 545, the power-providing components may power the light-emitting components (e.g., the LEDs) by charging the capacitor to VLED.

At 550, the wearable device may drive the LEDs according to the LED configuration and using the input voltage VLED (e.g., by discharging the capacitor from the input voltage VLED). For example, the wearable device may drive the LEDs to emit light 555 in accordance with the LED configuration, where the light 555 is used to acquire physiological data throughout the measurement interval. The capacitor may discharge during the pulse instances of the measurement pattern and recharge during the settling periods of the measurement pattern. By driving the LEDs (e.g., and receiving signals from the LEDs via the light-receiving components), the wearable device may acquire physiological data (e.g., PPG data) from the user during the measurement interval. In some examples, the wearable device may repeat the operations 535, 540, 545, and 550 one or more times during one or more charging durations and subsequent measurement intervals according to one or more of the set of LED configurations and corresponding VLEDs.

FIG. 6 shows a flowchart illustrating a method 600 that supports dynamic light emitting diode voltage control for wearable devices in accordance with aspects of the present disclosure. The operations of the method 600 may be implemented by a wearable device or its components as described herein. For example, the operations of the method 600 may be performed by a wearable device as described with reference to FIGS. 1 through 5. In some examples, a wearable device may execute a set of instructions to control the functional elements of the wearable device to perform the described functions. Additionally, or alternatively, the wearable device may perform aspects of the described functions using special-purpose hardware.

At 605, the method may include identifying a light-emitting configuration usable by one or more light-emitting components of the wearable device to acquire physiological data from a user throughout a measurement interval, the light-emitting configuration comprising a drive current associated with the one or more light-emitting components, a current provided to the one or more light-emitting components during the measurement interval, a measurement pattern throughout the measurement interval, or any combination thereof. The operations of 605 may be performed in accordance with examples as disclosed herein.

At 610, the method may include determining a minimum anode voltage of an anode line coupled with the one or more light-emitting components that enables the one or more light-emitting components to acquire physiological data throughout the measurement interval based at least in part on the light-emitting configuration, wherein an anode voltage of the anode line is based at least in part on an input voltage of a power input line coupled with a battery of the wearable device. The operations of 610 may be performed in accordance with examples as disclosed herein.

At 615, the method may include calculating, for the light-emitting configuration, a starting input voltage of the power input line based at least in part on the minimum anode voltage. The operations of 615 may be performed in accordance with examples as disclosed herein.

At 620, the method may include causing a power supply (e.g., the battery, a converter of the electronic circuitry, or both) to charge the power input line to at least the starting input voltage prior to the measurement interval. The operations of 620 may be performed in accordance with examples as disclosed herein.

At 625, the method may include acquiring physiological data from the user during the measurement interval using the one or more light-emitting components based at least in part on charging the power input line to at least the starting input voltage. The operations of 625 may be performed in accordance with examples as disclosed herein.

It should be noted that the methods described above describe possible implementations, and that the operations and the steps may be rearranged or otherwise modified and that other implementations are possible. Furthermore, aspects from two or more of the methods may be combined.

A method by an apparatus is described. The method may include one or more sensors configured to acquire physiological data from a user, the one or more sensors comprising one or more light-emitting components, a power supply configured to provide power to the one or more sensors, electronic circuitry configured to electrically couple the power supply with the one or more light-emitting components, the electronic circuitry comprising a power input line and an anode line, wherein the one or more light-emitting components are coupled with the anode line, and wherein an anode voltage of the anode line is based at least in part on an input voltage of the power input line, one or more processors communicatively coupled with the power supply and the one or more sensors, wherein the one or more processors are configured to, identify a light-emitting configuration usable by the one or more light-emitting components to acquire physiological data from the user throughout a measurement interval, the light-emitting configuration comprising a drive current associated with the one or more light-emitting components, a current provided to the one or more light-emitting components during the measurement interval, a measurement pattern throughout the measurement interval, or any combination thereof, determine a minimum anode voltage of the anode line that enables the one or more light-emitting components to acquire physiological data throughout the measurement interval based at least in part on the light-emitting configuration, calculate, for the light-emitting configuration, a starting input voltage of the power input line based at least in part on the minimum anode voltage, cause the power supply (e.g., battery, a converter of the electronic circuitry, or both) to charge the power input line to at least the starting input voltage prior to the measurement interval, and acquire physiological data from the user during the measurement interval using the one or more light-emitting components based at least in part on charging the power input line to at least the starting input voltage.

An apparatus is described. The apparatus may include one or more memories storing processor executable code, and one or more processors coupled with the one or more memories. The one or more processors may individually or collectively be operable to execute the code to cause the apparatus to one or more sensors configure to acquire physiological data from a user, the one or more sensors comprising one or more light-emitting components, a battery configure to provide power to the one or more sensors, electronic circuitry configure to electrically couple the battery with the one or more light-emitting components, the electronic circuitry comprising a power input line and an anode line, wherein the one or more light-emitting components are coupled with the anode line, and wherein an anode voltage of the anode line is based at least in part on an input voltage of the power input line, one or more processors communicatively couple with the battery and the one or more sensors, wherein the one or more processors are configured to, identify a light-emitting configuration usable by the one or more light-emitting components to acquire physiological data from the user throughout a measurement interval, the light-emitting configuration comprising a drive current associated with the one or more light-emitting components, a current provided to the one or more light-emitting components during the measurement interval, a measurement pattern throughout the measurement interval, or any combination thereof, determine a minimum anode voltage of the anode line that enables the one or more light-emitting components to acquire physiological data throughout the measurement interval based at least in part on the light-emitting configuration, calculate, for the light-emitting configuration, a starting input voltage of the power input line based at least in part on the minimum anode voltage, cause the battery to charge the power input line to at least the starting input voltage prior to the measurement interval, and acquire physiological data from the user during the measurement interval using the one or more light-emitting components based at least in part on charging the power input line to at least the starting input voltage.

Another apparatus is described. The apparatus may include means for one or more sensors configured to acquire physiological data from a user, the one or more sensors comprising one or more light-emitting components, means for a battery configured to provide power to the one or more sensors, means for electronic circuitry configured to electrically couple the battery with the one or more light-emitting components, the electronic circuitry comprising a power input line and an anode line, wherein the one or more light-emitting components are coupled with the anode line, and wherein an anode voltage of the anode line is based at least in part on an input voltage of the power input line, means for one or more processors communicatively coupled with the battery and the one or more sensors, wherein the one or more processors are configured to, means for identify a light-emitting configuration usable by the one or more light-emitting components to acquire physiological data from the user throughout a measurement interval, the light-emitting configuration comprising a drive current associated with the one or more light-emitting components, a current provided to the one or more light-emitting components during the measurement interval, a measurement pattern throughout the measurement interval, or any combination thereof, means for determine a minimum anode voltage of the anode line that enables the one or more light-emitting components to acquire physiological data throughout the measurement interval based at least in part on the light-emitting configuration, means for calculate, for the light-emitting configuration, a starting input voltage of the power input line based at least in part on the minimum anode voltage, means for cause the battery, a converter of the electronic circuitry, or both, to charge the power input line to at least the starting input voltage prior to the measurement interval, and means for acquire physiological data from the user during the measurement interval using the one or more light-emitting components based at least in part on charging the power input line to at least the starting input voltage.

A non-transitory computer-readable medium storing code is described. The code may include instructions executable by one or more processors to one or more sensors configure to acquire physiological data from a user, the one or more sensors comprising one or more light-emitting components, a battery configure to provide power to the one or more sensors, electronic circuitry configure to electrically couple the battery with the one or more light-emitting components, the electronic circuitry comprising a power input line and an anode line, wherein the one or more light-emitting components are coupled with the anode line, and wherein an anode voltage of the anode line is based at least in part on an input voltage of the power input line, one or more processors communicatively couple with the battery and the one or more sensors, wherein the one or more processors are configured to, identify a light-emitting configuration usable by the one or more light-emitting components to acquire physiological data from the user throughout a measurement interval, the light-emitting configuration comprising a drive current associated with the one or more light-emitting components, a current provided to the one or more light-emitting components during the measurement interval, a measurement pattern throughout the measurement interval, or any combination thereof, determine a minimum anode voltage of the anode line that enables the one or more light-emitting components to acquire physiological data throughout the measurement interval based at least in part on the light-emitting configuration, calculate, for the light-emitting configuration, a starting input voltage of the power input line based at least in part on the minimum anode voltage, cause the battery to charge the power input line to at least the starting input voltage prior to the measurement interval, and acquire physiological data from the user during the measurement interval using the one or more light-emitting components based at least in part on charging the power input line to at least the starting input voltage.

Some examples of the method, apparatus, and non-transitory computer-readable medium described herein may further include operations, features, means, or instructions for identify an additional light-emitting configuration usable by the one or more light-emitting components to acquire physiological data from the user throughout an additional measurement interval, determine an additional minimum anode voltage of the anode line that enables the one or more light-emitting components to acquire physiological data throughout the additional measurement interval based at least in part on the additional light-emitting configuration, calculate, for the additional light-emitting configuration, an additional starting input voltage of the power input line based at least in part on the additional minimum anode voltage, cause the battery, a converter of the electronic circuitry, or both, to charge the power input line to at least the additional starting input voltage prior to the additional measurement interval, and acquire additional physiological data from a user during the additional measurement interval using the one or more light-emitting components based at least in part on charging the power input line to at least the additional starting input voltage.

In some examples of the method, apparatus, and non-transitory computer-readable medium described herein, wherein the measurement interval may be associated with a first charging duration prior to the measurement interval that the power input line may be charged to at least the starting input voltage and wherein the additional measurement interval may be associated with an additional charging duration prior to the additional measurement interval that the power input line may be charged to at least the additional starting input voltage, wherein the first charging duration and the additional charging duration may be different based at least in part on the starting input voltage and the additional starting input voltage being different.

Some examples of the method, apparatus, and non-transitory computer-readable medium described herein may further include operations, features, means, or instructions for perform one or more simulations to model the anode voltage of the anode line throughout the measurement interval based at least in part on the measurement pattern of the light-emitting configuration, wherein determining the minimum anode voltage of the anode line, calculating the starting input voltage, or both, may be based at least in part on the one or more simulations.

In some examples of the method, apparatus, and non-transitory computer-readable medium described herein, and the method, apparatuses, and non-transitory computer-readable medium may include further operations, features, means, or instructions for simulate one or more voltage decreases in the anode voltage of the anode line during the one or more pulsing instances of the measurement pattern and simulate one or more voltage increases in the anode voltage of the anode line during the one or more settling periods of the measurement pattern, wherein determining the minimum anode voltage of the anode line, calculating the starting input voltage, or both, may be based at least in part on simulating the one or more voltage decreases, the one or more voltage increases, or both.

In some examples of the method, apparatus, and non-transitory computer-readable medium described herein, the light-emitting configuration further comprises a settling period of the one or more light-emitting components between one or more pulsing instances, a burn time of the one or more pulsing instances, one or more wavelengths of light used by the one or more light-emitting components during the measurement interval, or any combination thereof.

Some examples of the method, apparatus, and non-transitory computer-readable medium described herein may further include operations, features, means, or instructions for determine a charging duration between the measurement interval and a previous measurement interval based at least in part on the starting input voltage, wherein the battery may be configured to charge the power input line to at least the starting input voltage during the charging duration.

In some examples of the method, apparatus, and non-transitory computer-readable medium described herein, the one or more light-emitting components may be connected to the anode line in parallel.

In some examples of the method, apparatus, and non-transitory computer-readable medium described herein, the electronic circuitry may include operations, features, means, or instructions for one or more resistors that electrically couple the battery power input line and the anode line, wherein the anode voltage of the anode line may be based at least in part on the input voltage of the power input line and a resistance of the one or more resistors.

In some examples of the method, apparatus, and non-transitory computer-readable medium described herein, the electronic circuitry may include operations, features, means, or instructions for one or more capacitors electrically coupled with the anode line, wherein the anode voltage of the anode line may be based at least in part on the input voltage of the power input line and a capacitance of the one or more capacitors, wherein the physiological data may be collected by powering the one or more light-emitting components using power stored in the one or more capacitors.

In some examples of the method, apparatus, and non-transitory computer-readable medium described herein, the wearable device comprises a wearable ring device.

In some examples of the method, apparatus, and non-transitory computer-readable medium described herein, the wearable device comprises a wrist-worn wearable device.

A method for operating a wearable device by an apparatus is described. The method may include identifying a light-emitting configuration usable by one or more light-emitting components of the wearable device to acquire physiological data from a user throughout a measurement interval, the light-emitting configuration comprising a drive current associated with the one or more light-emitting components, a current provided to the one or more light-emitting components during the measurement interval, a measurement pattern throughout the measurement interval, or any combination thereof, determining a minimum anode voltage of an anode line coupled with the one or more light-emitting components that enables the one or more light-emitting components to acquire physiological data throughout the measurement interval based at least in part on the light-emitting configuration, wherein an anode voltage of the anode line is based at least in part on an input voltage of a power input line coupled with a battery of the wearable device, calculating, for the light-emitting configuration, a starting input voltage of the power input line based at least in part on the minimum anode voltage, causing the battery to charge the power input line to at least the starting input voltage prior to the measurement interval, and acquiring physiological data from the user during the measurement interval using the one or more light-emitting components based at least in part on charging the power input line to at least the starting input voltage.

An apparatus for operating a wearable device is described. The apparatus may include one or more memories storing processor executable code, and one or more processors coupled with the one or more memories. The one or more processors may individually or collectively be operable to execute the code to cause the apparatus to identify a light-emitting configuration usable by one or more light-emitting components of the wearable device to acquire physiological data from a user throughout a measurement interval, the light-emitting configuration comprising a drive current associated with the one or more light-emitting components, a current provided to the one or more light-emitting components during the measurement interval, a measurement pattern throughout the measurement interval, or any combination thereof, determine a minimum anode voltage of an anode line coupled with the one or more light-emitting components that enables the one or more light-emitting components to acquire physiological data throughout the measurement interval based at least in part on the light-emitting configuration, wherein an anode voltage of the anode line is based at least in part on an input voltage of a power input line coupled with a battery of the wearable device, calculate, for the light-emitting configuration, a starting input voltage of the power input line based at least in part on the minimum anode voltage, cause the battery to charge the power input line to at least the starting input voltage prior to the measurement interval, and acquire physiological data from the user during the measurement interval using the one or more light-emitting components based at least in part on charging the power input line to at least the starting input voltage.

Another apparatus for operating a wearable device is described. The apparatus may include means for identifying a light-emitting configuration usable by one or more light-emitting components of the wearable device to acquire physiological data from a user throughout a measurement interval, the light-emitting configuration comprising a drive current associated with the one or more light-emitting components, a current provided to the one or more light-emitting components during the measurement interval, a measurement pattern throughout the measurement interval, or any combination thereof, means for determining a minimum anode voltage of an anode line coupled with the one or more light-emitting components that enables the one or more light-emitting components to acquire physiological data throughout the measurement interval based at least in part on the light-emitting configuration, wherein an anode voltage of the anode line is based at least in part on an input voltage of a power input line coupled with a battery of the wearable device, means for calculating, for the light-emitting configuration, a starting input voltage of the power input line based at least in part on the minimum anode voltage, means for causing the battery to charge the power input line to at least the starting input voltage prior to the measurement interval, and means for acquiring physiological data from the user during the measurement interval using the one or more light-emitting components based at least in part on charging the power input line to at least the starting input voltage.

A non-transitory computer-readable medium storing code for operating a wearable device is described. The code may include instructions executable by one or more processors to identify a light-emitting configuration usable by one or more light-emitting components of the wearable device to acquire physiological data from a user throughout a measurement interval, the light-emitting configuration comprising a drive current associated with the one or more light-emitting components, a current provided to the one or more light-emitting components during the measurement interval, a measurement pattern throughout the measurement interval, or any combination thereof, determine a minimum anode voltage of an anode line coupled with the one or more light-emitting components that enables the one or more light-emitting components to acquire physiological data throughout the measurement interval based at least in part on the light-emitting configuration, wherein an anode voltage of the anode line is based at least in part on an input voltage of a power input line coupled with a battery of the wearable device, calculate, for the light-emitting configuration, a starting input voltage of the power input line based at least in part on the minimum anode voltage, cause the battery, a converter of the electronic circuitry, or both, to charge the power input line to at least the starting input voltage prior to the measurement interval, and acquire physiological data from the user during the measurement interval using the one or more light-emitting components based at least in part on charging the power input line to at least the starting input voltage.

Some examples of the method, apparatus, and non-transitory computer-readable medium described herein may further include operations, features, means, or instructions for identifying an additional light-emitting configuration usable by the one or more light-emitting components to acquire physiological data from the user throughout an additional measurement interval, determining an additional minimum anode voltage of the anode line that enables the one or more light-emitting components to acquire physiological data throughout the additional measurement interval based at least in part on the additional light-emitting configuration, calculating, for the additional light-emitting configuration, an additional starting input voltage of the power input line based at least in part on the additional minimum anode voltage, causing the battery to charge the power input line to at least the additional starting input voltage prior to the additional measurement interval, and acquiring additional physiological data from a user during the additional measurement interval using the one or more light-emitting components based at least in part on charging the power input line to at least the additional starting input voltage.

In some examples of the method, apparatus, and non-transitory computer-readable medium described herein, wherein the measurement interval may be associated with a first charging duration prior to the measurement interval that the power input line may be charged to at least the starting input voltage and wherein the additional measurement interval may be associated with an additional charging duration prior to the additional measurement interval that the power input line may be charged to at least the additional starting input voltage, wherein the first charging duration and the additional charging duration may be different based at least in part on the starting input voltage and the additional starting input voltage being different.

Some examples of the method, apparatus, and non-transitory computer-readable medium described herein may further include operations, features, means, or instructions for performing one or more simulations to model the anode voltage of the anode line throughout the measurement interval based at least in part on the measurement pattern of the light-emitting configuration, wherein determining the minimum anode voltage of the anode line, calculating the starting input voltage, or both, may be based at least in part on the one or more simulations.

In some examples of the method, apparatus, and non-transitory computer-readable medium described herein, the measurement pattern of the light-emitting configuration comprises one or more pulsing instances that the one or more light-emitting components emit light and the method, apparatuses, and non-transitory computer-readable medium may include further operations, features, means, or instructions for simulating one or more voltage decreases in the anode voltage of the anode line during the one or more pulsing instances of the measurement pattern and simulating one or more voltage increases in the anode voltage of the anode line during the one or more settling periods of the measurement pattern, wherein determining the minimum anode voltage of the anode line, calculating the starting input voltage, or both, may be based at least in part on simulating the one or more voltage decreases, the one or more voltage increases, or both.

In some examples of the method, apparatus, and non-transitory computer-readable medium described herein, the light-emitting configuration further comprises a settling period of the one or more light-emitting components between one or more pulsing instances, a burn time of the one or more pulsing instances, one or more wavelengths of light used by the one or more light-emitting components during the measurement interval, or any combination thereof.

Some examples of the method, apparatus, and non-transitory computer-readable medium described herein may further include operations, features, means, or instructions for determining a charging duration between the measurement interval and a previous measurement interval based at least in part on the starting input voltage, wherein the battery may be configured to charge the power input line to at least the starting input voltage during the charging duration.

In some examples of the method, apparatus, and non-transitory computer-readable medium described herein, the one or more light-emitting components may be connected to the anode line in parallel.

In some examples of the method, apparatus, and non-transitory computer-readable medium described herein, the wearable device further comprises one or more resistors that electrically couple the power input line and the anode line and the anode voltage of the anode line may be based at least in part on the input voltage of the power input line and a resistance of the one or more resistors.

In some examples of the method, apparatus, and non-transitory computer-readable medium described herein, the wearable device further comprises one or more capacitors electrically coupled with the anode line, the anode voltage of the anode line may be based at least in part on the input voltage of the power input line and a capacitance of the one or more capacitors, and the physiological data may be collected by powering the one or more light-emitting components using power stored in the one or more capacitors.

In some examples of the method, apparatus, and non-transitory computer-readable medium described herein, the wearable device comprises a wearable ring device.

In some examples of the method, apparatus, and non-transitory computer-readable medium described herein, the wearable device comprises a wrist-worn wearable device.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A wearable device, comprising:

one or more sensors configured to acquire physiological data associated with one or more measurement types from a user, the one or more sensors comprising one or more light-emitting components and one or more light-receiving components;

a power supply configured to provide power to the one or more sensors;

electronic circuitry configured to electrically couple the power supply with the one or more light-emitting components, the electronic circuitry comprising a power input line and an anode line, wherein the one or more light-emitting components are coupled with the anode line, and wherein an anode voltage of the anode line is based at least in part on an input voltage of the power input line; and one or more processors communicatively coupled with the power supply and the one or more sensors, wherein the one or more processors are configured to:

identify a light-emitting configuration from a plurality of light-emitting configurations usable by the one or more light-emitting components to acquire physiological data from the user throughout a measurement interval, wherein the light-emitting configuration is based at least in part on the one or more measurement types associated with the physiological data, and wherein the light-emitting configuration comprises a drive current associated with the one or more light-emitting components, a current provided to the one or more light-emitting components during the measurement interval, a measurement pattern throughout the measurement interval, or any combination thereof;

determine a minimum anode voltage of the anode line that enables the one or more light-emitting components to acquire the physiological data throughout the measurement interval based at least in part on the light-emitting configuration;

calculate, for the light-emitting configuration, a starting input voltage of the power input line based at least in part on the minimum anode voltage;

cause the power supply to charge the anode line to at least the starting input voltage prior to the measurement interval; and acquire the physiological data associated with the one or more measurement types from the user during the measurement interval using the one or more light-emitting components based at least in part on charging the anode line to at least the starting input voltage.

2. The wearable device of claim 1, wherein the one or more processors are further configured to:

identify an additional light-emitting configuration from the plurality of light-emitting configurations usable by the one or more light-emitting components to acquire physiological data from the user throughout an additional measurement interval;

determine an additional minimum anode voltage of the anode line that enables the one or more light-emitting components to acquire the physiological data throughout the additional measurement interval based at least in part on the additional light-emitting configuration;

calculate, for the additional light-emitting configuration, an additional starting input voltage of the power input line based at least in part on the additional minimum anode voltage;

cause the power supply to charge the anode line to at least the additional starting input voltage prior to the additional measurement interval; and acquire additional physiological data from the user during the additional measurement interval using the one or more light-emitting components based at least in part on charging the anode line to at least the additional starting input voltage.

3. The wearable device of claim 2, wherein the measurement interval is associated with a first charging duration prior to the measurement interval that the anode line is charged to at least the starting input voltage, and wherein the additional measurement interval is associated with an additional charging duration prior to the additional measurement interval that the anode line is charged to at least the additional starting input voltage, wherein the first charging duration and the additional charging duration are different based at least in part on the starting input voltage and the additional starting input voltage being different.

4. The wearable device of claim 1, wherein the one or more processors are further configured to:

perform one or more simulations to model the anode voltage of the anode line throughout the measurement interval based at least in part on the measurement pattern of the light-emitting configuration, wherein determining the minimum anode voltage of the anode line, calculating the starting input voltage, or both, is based at least in part on the one or more simulations.

5. The wearable device of claim 4, wherein the measurement pattern of the light-emitting configuration comprises one or more pulsing instances that the one or more light-emitting components emit light, and one or more settling periods that the one or more light-emitting components are inactive, wherein, to perform the one or more simulations, the one or more processors are configured to:

simulate one or more voltage decreases in the anode voltage of the anode line during the one or more pulsing instances of the measurement pattern; and simulate one or more voltage increases in the anode voltage of the anode line during the one or more settling periods of the measurement pattern, wherein determining the minimum anode voltage of the anode line, calculating the starting input voltage, or both, is based at least in part on simulating the one or more voltage decreases, the one or more voltage increases, or both.

6. The wearable device of claim 1, wherein the light-emitting configuration further comprises a settling period of the one or more light-emitting components between one or more pulsing instances, a burn time of the one or more pulsing instances, one or more wavelengths of light used by the one or more light-emitting components during the measurement interval, or any combination thereof.

7. The wearable device of claim 1, wherein the one or more processors are further configured to:

determine a charging duration between the measurement interval and a previous measurement interval based at least in part on the starting input voltage, wherein the power supply is configured to charge the anode line to at least the starting input voltage during the charging duration.

8. The wearable device of claim 1, wherein the one or more light-emitting components are connected to the anode line in parallel.

9. The wearable device of claim 1, wherein the electronic circuitry further comprises:

one or more resistors that electrically couple the power input line and the anode line, wherein the anode voltage of the anode line is based at least in part on the input voltage of the power input line and a resistance of the one or more resistors.

10. The wearable device of claim 1, wherein the electronic circuitry further comprises:

one or more capacitors electrically coupled with the anode line, wherein the anode voltage of the anode line is based at least in part on the input voltage of the power input line and a capacitance of the one or more capacitors, wherein the physiological data is collected by powering the one or more light-emitting components using power stored in the one or more capacitors.

11. The wearable device of claim 1, wherein the one or more processors are configured to:

perform one or more physiological measurements using the one or more light-emitting components and the one or more light-receiving components; and determine one or more parameters of the light-emitting configuration based at least in part on a signal received by the one or more light-receiving components during the one or more physiological measurements.

12. The wearable device of claim 1, wherein the wearable device comprises a wearable ring device.

13. The wearable device of claim 1, wherein the wearable device comprises a wrist-worn wearable device.

14. A method for operating a wearable device, comprising:

identifying a light-emitting configuration from a plurality of light-emitting configurations usable by one or more light-emitting components of the wearable device to acquire physiological data from a user throughout a measurement interval, wherein the light-emitting configuration is based at least in part on one or more measurement types associated with the physiological data, and wherein the light-emitting configuration comprises a drive current associated with the one or more light-emitting components, a current provided to the one or more light-emitting components during the measurement interval, a measurement pattern throughout the measurement interval, or any combination thereof;

determining a minimum anode voltage of an anode line coupled with the one or more light-emitting components that enables the one or more light-emitting components to acquire the physiological data throughout the measurement interval based at least in part on the light-emitting configuration, wherein an anode voltage of the anode line is based at least in part on an input voltage of a power input line coupled with a power supply of the wearable device;

calculating, for the light-emitting configuration, a starting input voltage of the power input line based at least in part on the minimum anode voltage;

causing the power supply to charge the anode line to at least the minimum anode voltage prior to the measurement interval based at least in part on the starting input voltage; and acquiring the physiological data associated with the one or more measurement types from the user during the measurement interval using the one or more light-emitting components based at least in part on charging the anode line to at least the minimum anode voltage.

15. The method of claim 14, further comprising:

identifying an additional light-emitting configuration from a plurality of light-emitting configurations usable by the one or more light-emitting components to acquire physiological data from the user throughout an additional measurement interval;

determining an additional minimum anode voltage of the anode line that enables the one or more light-emitting components to acquire the physiological data throughout the additional measurement interval based at least in part on the additional light-emitting configuration;

calculating, for the additional light-emitting configuration, an additional starting input voltage of the power input line based at least in part on the additional minimum anode voltage;

causing the power supply to charge the anode line to at least the additional starting input voltage prior to the additional measurement interval; and acquiring additional physiological data from the user during the additional measurement interval using the one or more light-emitting components based at least in part on charging the anode line to at least the additional starting input voltage.

16. The method of claim 15, wherein the measurement interval is associated with a first charging duration prior to the measurement interval that the anode line is charged to at least the starting input voltage, and wherein the additional measurement interval is associated with an additional charging duration prior to the additional measurement interval that the anode line is charged to at least the additional starting input voltage, wherein the first charging duration and the additional charging duration are different based at least in part on the starting input voltage and the additional starting input voltage being different.

17. The method of claim 14, further comprising:

performing one or more simulations to model the anode voltage of the anode line throughout the measurement interval based at least in part on the measurement pattern of the light-emitting configuration, wherein determining the minimum anode voltage of the anode line, calculating the starting input voltage, or both, is based at least in part on the one or more simulations.

18. The method of claim 14, wherein the measurement pattern of the light-emitting configuration comprises one or more pulsing instances that the one or more light-emitting components emit light, and one or more settling periods that the one or more light-emitting components are inactive, the method further comprising:

simulating one or more voltage decreases in the anode voltage of the anode line during the one or more pulsing instances of the measurement pattern; and simulating one or more voltage increases in the anode voltage of the anode line during the one or more settling periods of the measurement pattern, wherein determining the minimum anode voltage of the anode line, calculating the starting input voltage, or both, is based at least in part on simulating the one or more voltage decreases, the one or more voltage increases, or both.

19. The method of claim 14, wherein the light-emitting configuration further comprises a settling period of the one or more light-emitting components between one or more pulsing instances, a burn time of the one or more pulsing instances, one or more wavelengths of light used by the one or more light-emitting components during the measurement interval, or any combination thereof.

20. The method of claim 14, further comprising:

determining a charging duration between the measurement interval and a previous measurement interval based at least in part on the starting input voltage, wherein the power supply is configured to charge the anode line to at least the starting input voltage during the charging duration.

* * * * *